(12) United States Patent
Neel et al.

(10) Patent No.: US 7,467,065 B2
(45) Date of Patent: Dec. 16, 2008

(54) COMPUTER INTERFACE FOR DIAGNOSTIC METER

(75) Inventors: Gary T. Neel, Weston, FL (US); Alex Sanchez, Miami Lks, FL (US)

(73) Assignee: Home Diagnostics, Inc., Ft. Lauderdale, FL (US)

( * ) Notice: Subject to any disclaimer, the term of this patent is extended or adjusted under 35 U.S.C. 154(b) by 661 days.

(21) Appl. No.: 11/118,494

(22) Filed: May 2, 2005

(65) Prior Publication Data

US 2006/0248398 A1 Nov. 2, 2006

(51) Int. Cl.
*G06F 11/00* (2006.01)

(52) U.S. Cl. .................. 702/183; 702/19; 714/33; 600/300; 600/365; 600/310

(58) Field of Classification Search .............. 702/19, 702/183, 90, 187; 600/300, 301, 365; 714/33
See application file for complete search history.

(56) References Cited

U.S. PATENT DOCUMENTS

| | | | | |
|---|---|---|---|---|
| 5,640,301 A * | 6/1997 | Roecker et al. | .............. | 361/686 |
| 6,131,125 A | 10/2000 | Rostoker et al. | | |
| 6,370,603 B1 | 4/2002 | Silverman et al. | | |
| 6,691,068 B1 * | 2/2004 | Freed et al. | .................. | 702/187 |
| 6,976,958 B2 * | 12/2005 | Quy | ............ | 600/301 |
| 7,156,809 B2 * | 1/2007 | Quy | ............ | 600/301 |
| 7,278,983 B2 * | 10/2007 | Ireland et al. | ............... | 604/66 |
| 7,344,500 B2 | 3/2008 | Talbot et al. | | |
| 2002/0129170 A1 * | 9/2002 | Moore et al. | ................ | 709/249 |
| 2002/0184055 A1 * | 12/2002 | Naghavi et al. | ............... | 705/2 |
| 2002/0193679 A1 | 12/2002 | Malave et al. | | |
| 2003/0060692 A1 * | 3/2003 | Ruchti et al. | ................ | 600/310 |
| 2005/0065464 A1 | 3/2005 | Talbot et al. | | |
| 2005/0080652 A1 | 4/2005 | Brown | | |
| 2005/0159787 A1 * | 7/2005 | Linberg et al. | ................ | 607/31 |
| 2006/0010014 A1 * | 1/2006 | Brown | ........................ | 705/2 |
| 2006/0154642 A1 * | 7/2006 | Scannell | .................. | 455/404.1 |
| 2006/0200007 A1 * | 9/2006 | Brockway et al. | ........... | 600/300 |
| 2007/0179398 A1 * | 8/2007 | Margolis | .................... | 600/559 |
| 2007/0233395 A1 * | 10/2007 | Neel et al. | .................... | 702/19 |

FOREIGN PATENT DOCUMENTS

WO    WO 01/63886 A2    8/2001

* cited by examiner

*Primary Examiner*—Carol S Tsai
(74) *Attorney, Agent, or Firm*—Finnegan, Henderson, Farabow, Garrett & Dunner, L.L.P.

(57) ABSTRACT

A smart interface assembly is provided which enables convenient, instant, and discreet communication between an analytical meter and a computer, the transfer of data from the analytical system, and/or the provision of interface software for the display or analysis of data. The smart interface assembly includes first and second couplings for interfacing with the personal computer and the analytical meter. The smart interface assembly has processing and memory capabilities facilitating displaying test results from an analytical system on a computer. The interface can also function as a storage device allowing transfer, access, or syncing of data from a diagnostic system to or by the personal computer without the need for special drivers, and also can facilitate communications between the diagnostic system and the computer using standard device drivers likely to be already present on the computer.

37 Claims, 12 Drawing Sheets

COMPUTER INTERFACE FOR DIAGNOSTIC METER

TECHNICAL FIELD

The present invention relates to the field of diagnostic testing and, more particularly, to diagnostic testing systems using electronic meters and digital communication.

BACKGROUND

Diagnostic testing systems are commonly used to perform various types of diagnostic tests on various types of samples. The diagnostic test may be a qualitative or quantitative test to determine the presence, concentration or amount of one or more analytes in a sample. However, the diagnostic test is not limited to the medical field. For instance, the diagnostic test may determine the presence or quantity of an analyte in water, soil, food products or other fluid or chemical sample.

Such diagnostic testing systems may include test media (e.g., a test strip, tab, disc, etc.) configured to react to the presence of the analyte in a sample, and a separate electronic meter configured to interface with the test media in order to conduct the diagnostic test and indicate the results of the diagnostic test to a user.

In order to conduct the diagnostic test, the user must first obtain sample test media, e.g., a test strip, from a container, then obtain a sample using a sampling device (e.g., by drawing blood using a lancet), and then apply the sample to the test media (either before or after inserting the test media into the meter interface). The meter then performs the diagnostic test on the sample and indicates the result to the user, e.g., using a numerical display. Most diagnostic meters have an onboard memory for storing results over a period of time so that trends can be identified from the test data. It is also known in the art to provide for the transfer of this data to a personal computer (e.g., an IBM compatible PC, an Apple Mac, etc.) using a data cable. A user may then use software pre-installed on the personal computer to analyze the data, or transmit the results to a physician so that an appropriate assessment of the patient's condition can be made. The pre-installed software includes drivers necessary to allow the diagnostic meter, which is a specialized device, to communicate with the PC.

It is well known that data, such as numerical values representing diagnostic test results, can be stored on removable media, such as floppy disks, CD-RW ROMs, flash drives, or other storage media of similar type. However, a difficulty can arise when a user desires to utilize a computer that does not have pre-installed drivers or analysis software. Further, the computer that the user wants to employ to analyze data may only permit software to be installed by system administrators, making it impossible to install the drivers or software application program for recognizing the meter, downloading and processing the user's data. Even if installation of software were permitted, valuable time would be wasted in troubleshooting or downloading additional software for reviewing the user's diagnostic test results. The practical result is that most users of diagnostics meters frequently do not submit to the inconvenience and complexity of using valuable analysis tools available through use of a computer, except perhaps, while at home.

Accordingly, there is a need for a diagnostic testing system whose hardware and software can work together to automatically configure a computer, assign resources, and allow for hardware configuration without complicated setup maneuvers.

SUMMARY

The present invention meets these and other needs by providing a diagnostic testing system having a meter for performing a diagnostic test on a sample applied to a test media and a smart, plug-and-play interface assembly capable of providing functionality including one or more of the following: i) auto-executable software for displaying test results from the meter attached to the computer; ii) a standalone storage device allowing the transfer, access or "syncing" of test data from the meter to or by a computer without the need for special drivers; and iii) an interface between a meter and a computer that allows communications therebetween using standard device drivers likely to be already present on a computer.

Plug and Play in Windows® based computers, as well as analogous Apple Mac protocols, allow a user to connect a hardware device and have the operating system configure and start the hardware. However, computer hardware, device drivers, and the operating system must all be in sync to allow installation without user intervention. For example, although Windows® provides plug-and-play functionality, if no device driver compatible with detected new hardware is available, the operating system cannot automatically configure and start the device. For this reason, prior art diagnostic meters require the user to first download and install device drivers before connecting the meter to the computer.

After a computer detects the connection of a new device, the operating system checks which hardware resources the device needs (such as interrupts, memory ranges, I/O ranges, and DMA channels) and assigns those resources. These requirements are derived from a hardware identification number provided by the device. The operating system then checks the availability of a driver that matches the hardware identification number of the device. The operating system will also choose among several drivers should more than one be identified.

If the device is not automatically installed by the operating system, the procedure becomes increasingly complicated as the operating system will request information about the device and where to find drivers. For non-standard devices, such as diagnostics meters, specialized drivers are required. Also, for networked computers under administrative control, such as those most frequently encountered in the workplace, and those generally available for public access, restricted privileges are required for a user to install or configure a specialized, non-standard device.

The present invention provides mechanisms for coupling a meter and a computer for communication without the requirement that the user perform any special set-up steps to auto-execute program files stored on the smart interface. To implement this plug-and-play functionality, the smart interface assembly of the present invention determines which communication protocols are required at each of its ports, and selects, activates, enables, or downloads the appropriate communication protocol drivers to enable proper operation. Data can be downloaded and stored from the meter onto a personal computer or stored on the smart interface assembly for viewing at a later, more convenient time.

In one exemplary embodiment of the invention, the smart interface assembly includes a first data coupling, a second data coupling, and an electrical cable connecting the first and second data couplings. The smart interface assembly can also include a circuit board, which can be mounted on a carrier. The data couplings can be connected by any known means, e.g., hard wired connections, connectors, plugs, or wireless devices (e.g., RF, IR, BlueTooth®, etc.).

According to one exemplary embodiment, the present invention can further include a plurality of electrical contacts, a protocol processor, and memory for electrically connecting to the first and second apparatuses (e.g. the meter and the personal computer). The protocol processor is capable of communicating with the first apparatus via the first data coupling and the second apparatus via the second data coupling. The data coupling, if not wireless, can include a ground contact and a voltage supply contact. If both data couplings are wireless, power can be provided to the circuitry of the smart interface device via batteries, capacitor(s), solar panel (s), a power supply or other known means.

In another exemplary embodiment of the invention, a user inserts a test strip into a meter to measure the amount of glucose in the blood. After an electronic meter performs one or more diagnostic tests, the data can be analyzed on a personal computer or transmitted to a physician's computer. A user first completes a connection between a computer and the first data coupling of the smart interface. This connection can be achieved via a Universal Serial Bus ("USB") connector IEEE-1394 plug, wireless link, or other known connection methods. The computer recognizes the interface, for example through Plug-and-Play protocols, and may execute interface software contained resident on the smart interface device, instructing the user to proceed. The user then completes a connection between the second data coupling and the data communication port of a meter in similar fashion. Once connected, the circuit of the smart interface handshakes with a processor within a microcontroller of the meter to execute machine language instructions and to complete the connection of the meter to the computer through the smart interface, for instance, through a protocol processor of the smart interface assembly. The protocol processor can auto-execute application program files stored in an onboard memory of the meter. The desired data is then transmitted from the memory directly to a processor within a microcontroller of the computer. The data can be optionally encrypted with device identification information, including a serial number of the meter, a user name, or other identifying data. Alternatively, the device and patient identification data can be transmitted from the meter together or sequentially, along with diagnostic test data, such that the computer software recognizes which data belongs with which user. The incoming data from the meter can then either be displayed on the computer's monitor or stored in a memory within the computer to be analyzed at a later time.

In another exemplary embodiment of the invention the user, optionally following prompts on the meter display, first completes a connection between the second data coupling with the data communication port of the meter. Once connected, the circuit of the smart interface handshakes with the electronics of the meter to complete the connection of the meter to the smart interface, for instance, through a protocol processor within the circuit board of the smart interface assembly. The meter and smart interface combination then form a composite device. Optionally, following a prompt on the meter display, the user then completes a connection between the first data coupling and the computer (e.g., USB port, IR port, BlueTooth® or RF antenna). The computer recognizes the smart interface and meter assembly, for example through. Plug-and-Play or other recognition protocols, and may execute interface software contained resident on the interface. For instance, the protocol processor can be configured to auto-execute application program files stored in a memory of the smart interface, or stored on a memory of the meter and communicated by the smart interface. As above, the desired data can then be transmitted from the meter's memory to the computer, and the data can either be displayed on the computer's monitor or otherwise stored. In this exemplary embodiment there is no need to store data in the interface device, but rather, the PC can interface with the meter's memory through the smart interface assembly.

In another exemplary embodiment, the smart interface and meter combination can contain hardware identification codes that signal to a computer, after completing a connection, that the combination device is a known device, e.g., a floppy drive. Naturally, a specialized pre-installed driver can be among those correlating the hardware identification code presented to the computer. By controlling the input and output of data to and from the device in a floppy-emulated fashion, the smart interface and meter combination can be readily interfaced with a computer using standard floppy device drivers, and can permit interfacing with a computer without special privileges. Floppy technology is long established, and implementations allow auto-execution of files which can provide for a straight-forward implementation of the invention. Additionally, the standard file allocation system used by floppy drives is reliable, and can be simply emulated to allow the smart interface and meter combination to access stored data as a normal file.

Additionally, present and future-developed implementations of various plug-and-play protocols and standard driver libraries can allow other input/output device drivers to be used without floppy emulation, such as flash drive drivers, PDA drivers, or even digital camera and media player drivers, etc., and this configuration is explained herein by means of example. Advantageously, operating systems choose an optimal driver from among various candidate drivers. Accordingly, the present invention enables various drivers to optimize the possibility of a successful interface.

In yet another exemplary embodiment, after an electronic meter performs one or more diagnostic tests, the test results can be transferred directly to a memory of the smart interface assembly. Although modern diagnostic meters can store weeks' or months' worth of data, storing some or all of the data on the memory of the smart interface assembly allows for outboard storage of test results. Furthermore, the user has an option of transporting the smart interface assembly, rather than the actual meter itself, to a computer for viewing results, providing a more discrete and convenient means for uploading and viewing results. For instance, a user can employ a computer in the workplace to view and analyze the test results, without having to directly interface the test meter with the computer. With the meter not connected, for example, the smart interface can be configured to provide a device identification code to the computer, identifying it as a mass storage device such as a flash drive, or other portable data carrier and behave accordingly. For example, software can run directly from the interface to analyze data resident thereon.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF EXEMPLARY EMBODIMENTS

Reference will now be made in detail to exemplary embodiments of the present invention, examples of which are illustrated in the accompanying drawings. Wherever possible, the same reference numbers will be used throughout the drawings to refer to the same or like parts. While the description includes exemplary embodiments, other embodiments are possible, and changes may be made to the embodiments described without departing from the spirit and scope of the invention. The following detailed description does not limit the invention. Instead, the scope of the invention is defined by the appended claims and their equivalents.

1. Smart Interface Assembly

Figure 1:
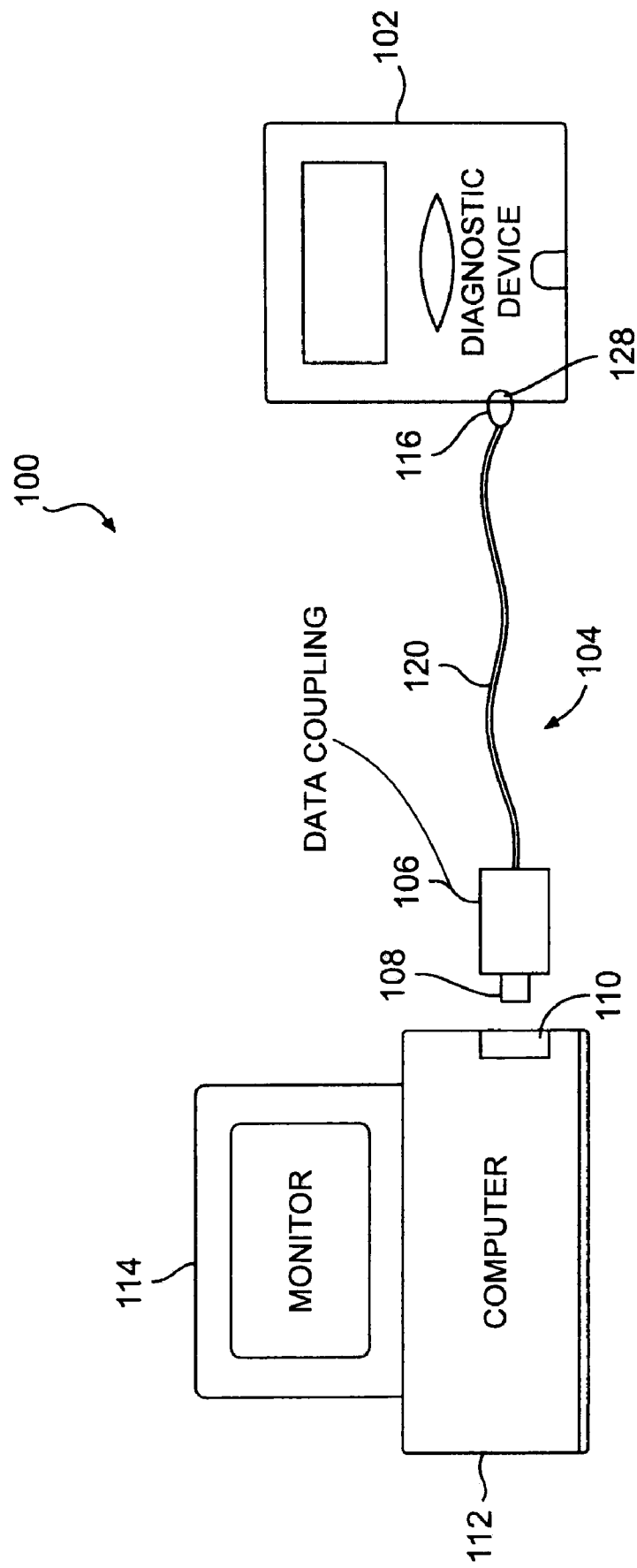
FIG. 1 is perspective view of a diagnostic testing system, in accordance with a preferred embodiment of the present invention.

FIG. 1 shows a diagnostic testing system 100 for conducting a diagnostic test in accordance with an exemplary embodiment of the present invention. Exemplary diagnostic testing system 100 includes a medical device 102, such as an electronic meter, configured to interface with test media to measure glucose levels in blood samples and indicate the results of the test to a user. Attached to the medical device 102 is a smart interface assembly 104, which includes an electric interface 120 with a first data coupling 106 and a second data coupling 116 attached at each end. The first data coupling 106 further comprises of a first plurality of pins 108, which can be inserted into a first port 110 of a computer 112. The second data coupling 116 can be inserted into a second port 128 of the medical device 102. Computer 112 processes and stores data received from the first data coupling 106 and further comprises a monitor 114 or any other output device for displaying the data, such as test results.

Figure 2:
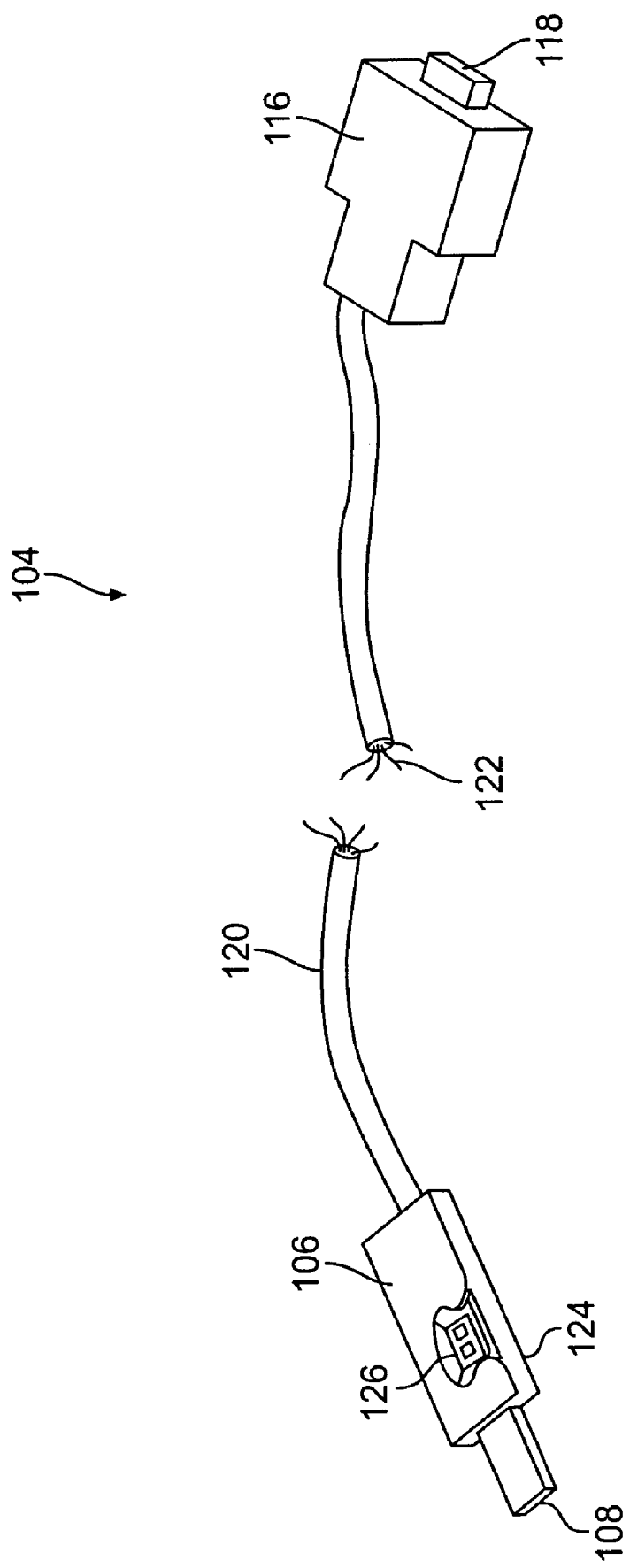
FIG. 2 is a perspective view of a smart interface assembly of FIG. 1, in accordance with the present invention.

FIG. 2 is a perspective view of the smart interface assembly 104, as shown in FIG. 1. Smart interface assembly 104 includes a first data coupling 106 having a first plurality of pins 108, a second data coupling 116 having a second plurality of pins 118, and an electrical interface 120 coupling the first data coupling 106 to the second data coupling 116. The electrical interface 120 can further include a number of conductors 122 for power, ground, and signals. The first data coupling 106 further comprises a carrier 124 with a circuit board 126 mounted within. Circuit board 126 is coupled to at least some of the wires of the electrical interface 120 at points between the free ends of the first plurality of pins 108 and the free ends of the second plurality of pins 118. The circuit board 126 can be formed as part of the smart interface assembly 104 rather than as a separate component, as described further below.

In the illustration of FIG. 2, the first data coupling 106 is a USB data coupling which connects to the first port 110, a USB port, within the computer 112. The second data coupling 116 is a data coupling which connects to the second port 128, a data port, within the medical device 102. Alternatively or in addition, there are several types of data couplings that are applicable to the method and apparatus of the present invention. In addition to USB and data couplings, there are Ethernet, Fire Wire, SCSI, modem, wireless, video, printer, serial data couplings, and several more. However, it will be understood that the present invention is not limited to any particular type of data coupling and that other data couplings may be employed consistent with the principles of the present invention.

Figure 9:
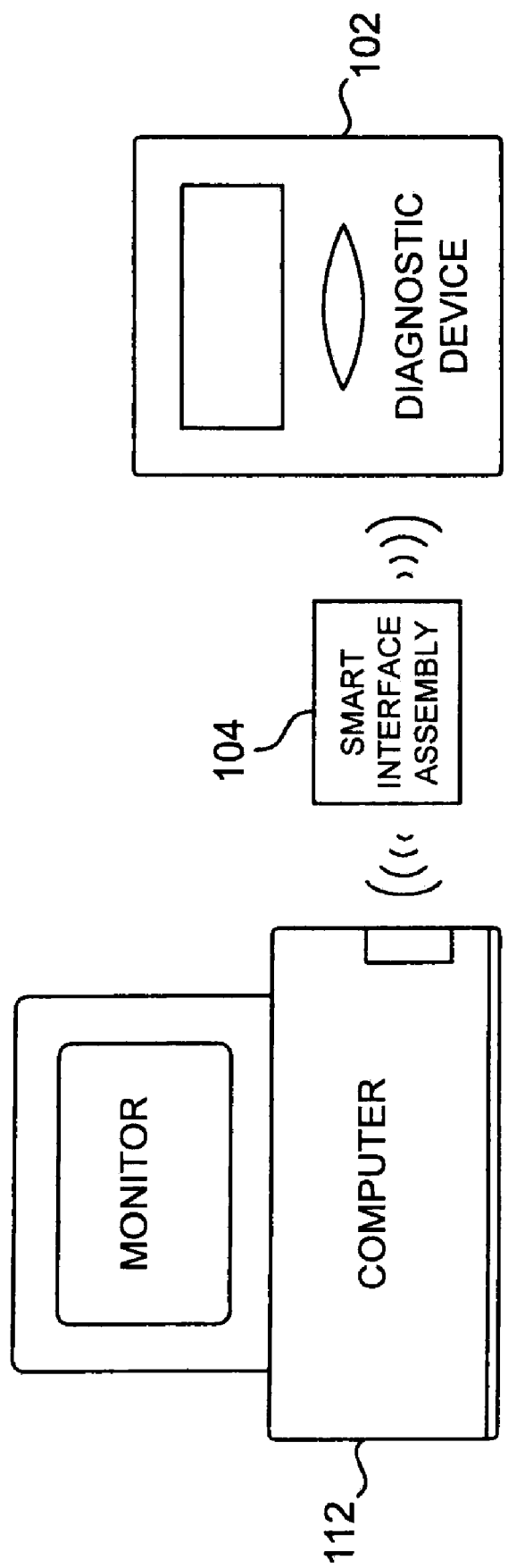
FIG. 9 illustrates a smart interface assembly with two wireless connections, in accordance with a preferred embodiment of the present invention.

As illustrated In FIGS. 9-12, the first and second data couplings 106, 116 may be connected by any known means, e.g., hard wired connections, connectors, plugs, or wireless devices. In one exemplary embodiment, FIG. 9 illustrates the smart interface assembly 104 with two wireless connections, one to the meter 102 and one to the computer 112. The wireless communications devices may be RF, IR, Blue-Tooth®, or other similar devices consistent with the principles of the present invention. The RF device can operate in a range of about 2.4 GHz to about 2.48 GHz and has an output in a range of about −30 to +20 dBm (100 mW). Furthermore, the RF device may be enabled for spread spectrum, frequency hopping, and full-duplex operation. In the frequency hopping operation, the RF device may be enabled for operation up to 1600 hops/sec, where a signal hops among 79 frequencies at 1 MHz intervals. Alternatively, the wireless communications device may be an IR device which operates on a wavelength in a range of about 850 nm to about 1050 nm.

Figure 10:
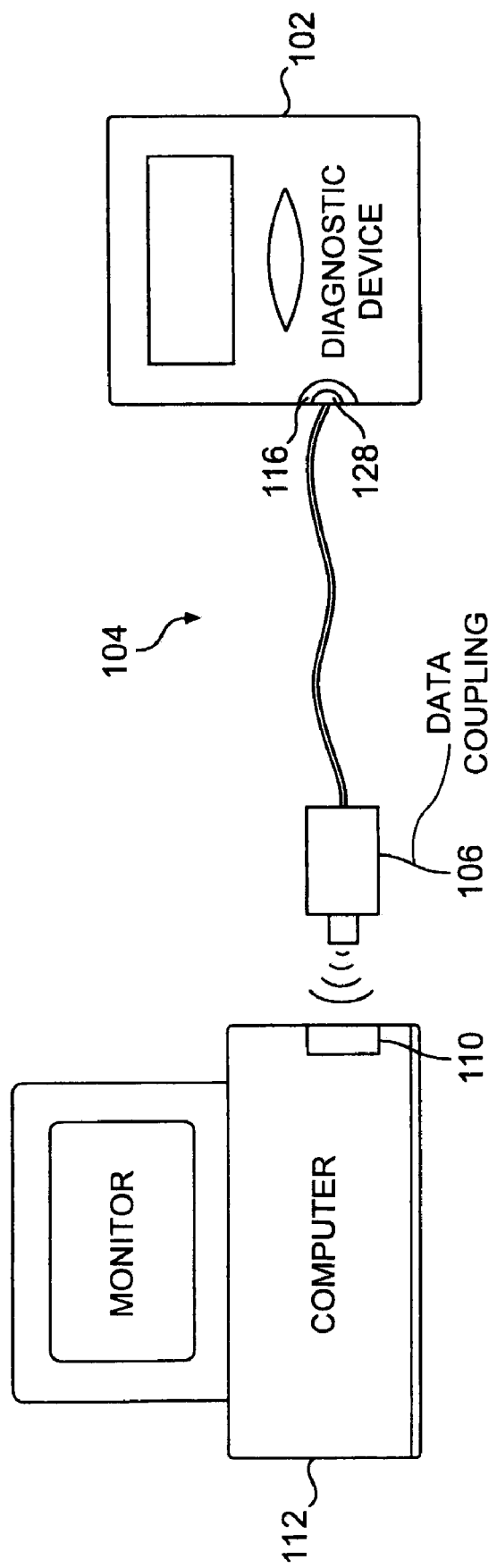
FIG. 10 illustrates a smart interface assembly hardwired into a meter and connected wirelessly to a computer, in accordance with a preferred embodiment of the present invention.

Alternatively, FIG. 10 illustrates the smart interface assembly 104 wherein a connection is hard wired between the data communication port 128 of the meter 102 and the second data coupling 116, and the first data coupling 106 is wirelessly connected to the computer 112.

Figure 11:
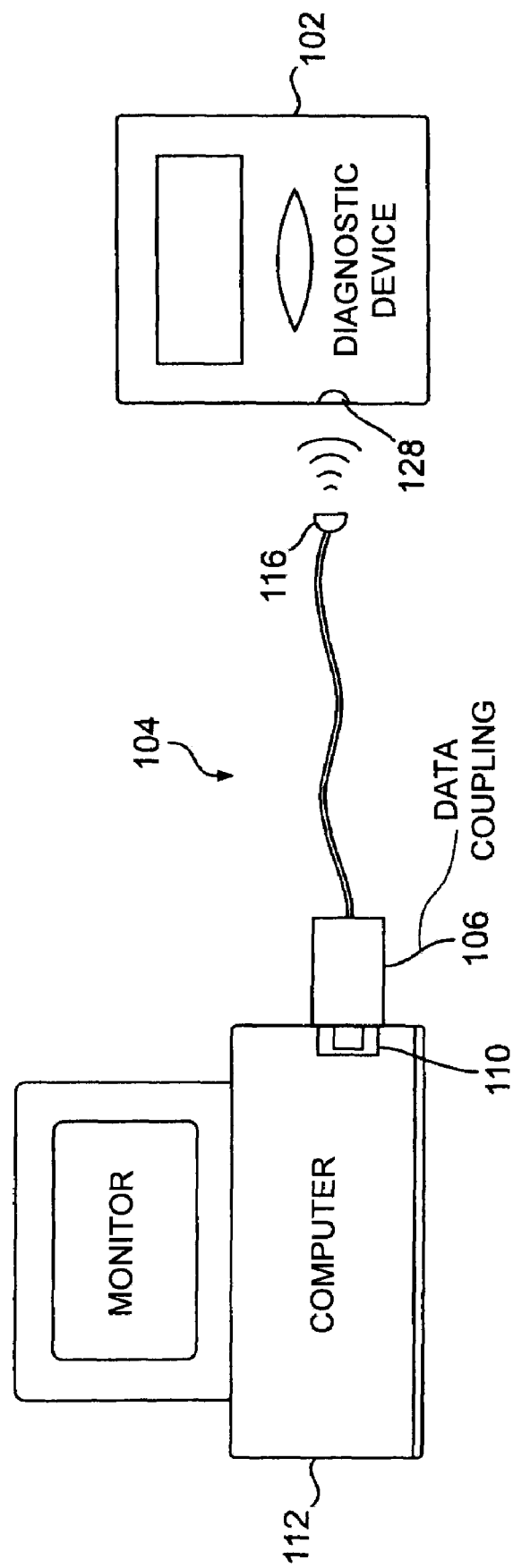
FIG. 11 is a smart interface assembly plugged into a computer and connected wirelessly to an electronic meter, in accordance with a preferred embodiment of the present invention.
Figure 12:
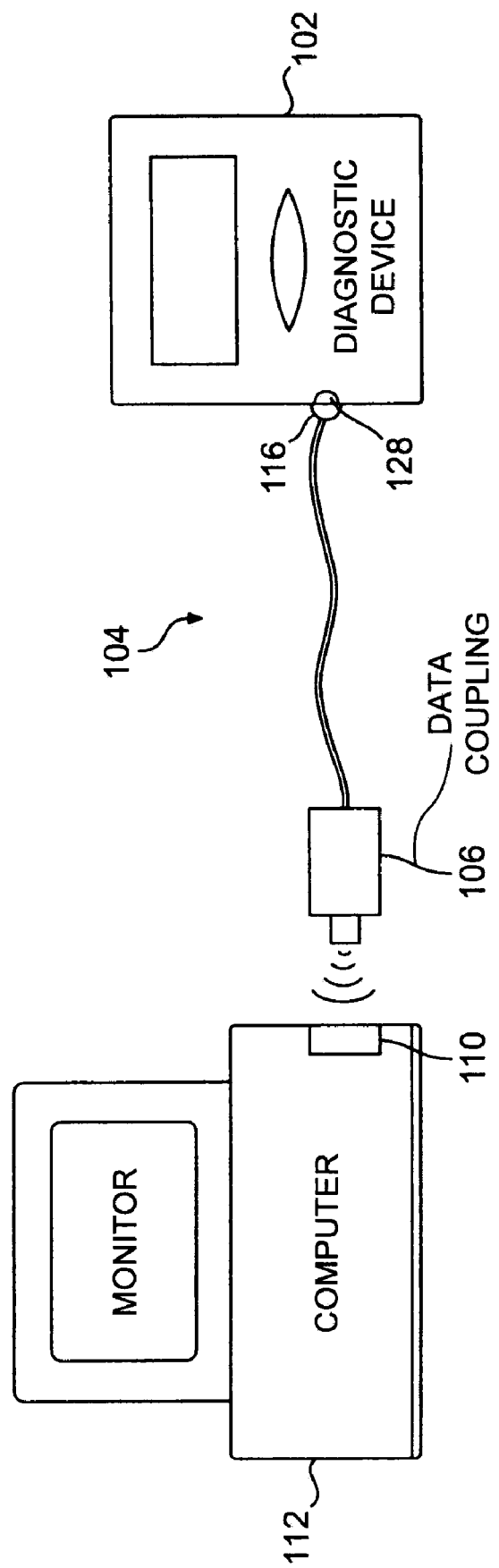
FIG. 12 illustrates a smart interface assembly plugged into a meter and connected wirelessly to a computer, in accordance with a preferred embodiment of the present invention.

With reference to FIG. 11, in the smart interface assembly 104 a connection is plugged in between the computer 112 and the first data coupling 106, and the second data coupling 116 is wirelessly connected to the meter 102. Alternatively, FIG. 12 illustrates the smart interface assembly 104 wherein a connection is plugged in between the data communication port 128 of the meter 102 and the second data coupling 116, and the first data coupling 106 is wirelessly connected to the computer 112. The plug may be a USB connector, IEEE 1394 connector, a serial connector, or another similar connector consistent with the principles of the present invention.

Figure 3:
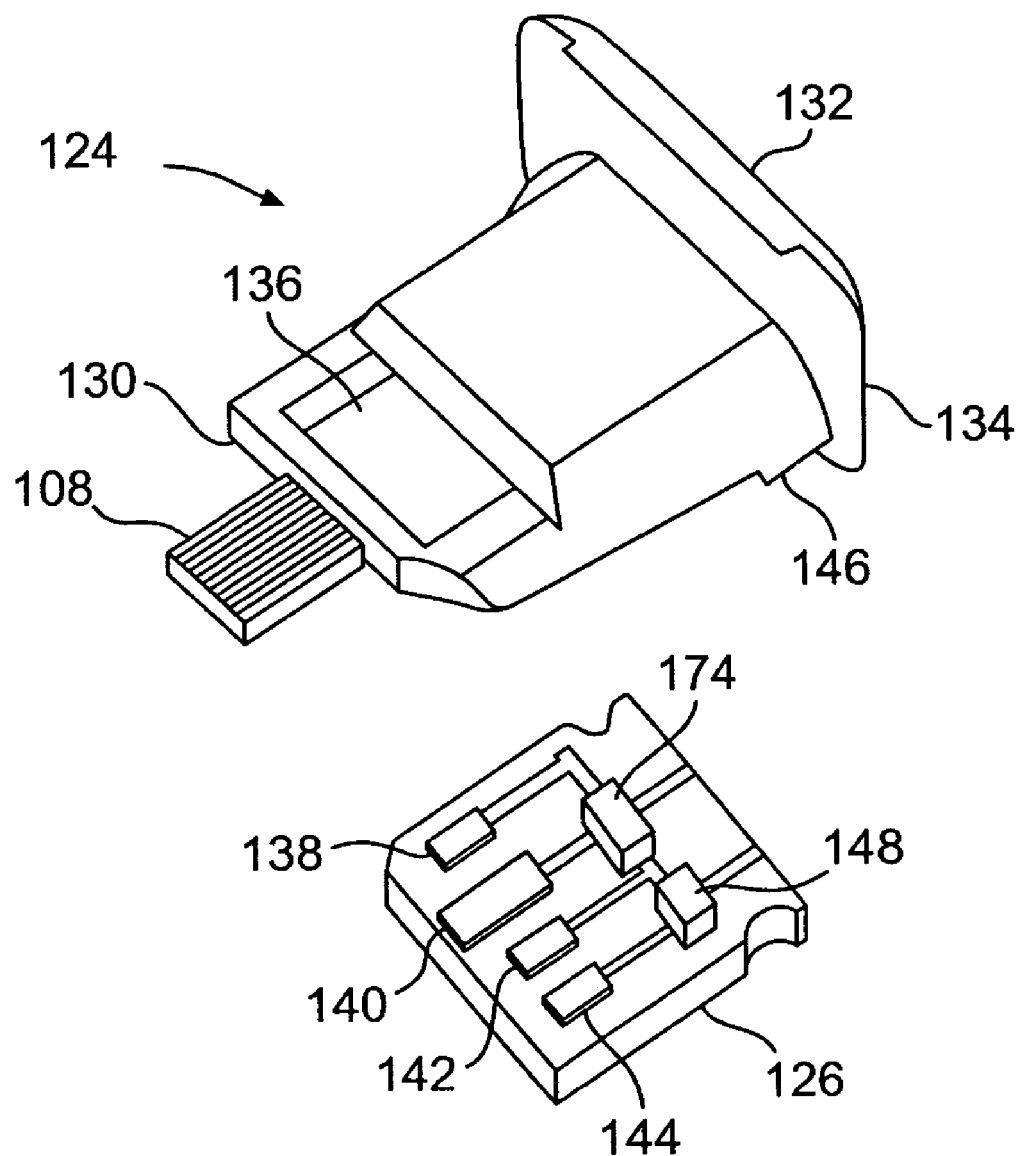
FIG. 3 illustrates a perspective view of a circuit board of FIG. 2, in accordance with a preferred embodiment of the present invention.

With reference to FIG. 3, the circuit board 126 of smart interface assembly 104 comprises a protocol processor 174 which houses the program logic of the interface assembly 104. Circuit board 126 is housed within the carrier 124 of the first data coupling 106. Carrier 124 includes a distal end 130 and a proximal end 132 and can be made out of a material such as plastics or resins, as known in the art. Further extending from the distal end 130 are the first plurality of pins 108 that are inserted into the first port 110 of the computer 112. Proximal end 132 may include a flange or knurl 134 to allow a user's fingers to grip the carrier 124 for either insertion into or removal from the first port 110. Carrier 124 can also include an opening 136 through which electrical contacts 138-144 are accessible.

Carrier 124 can further have a "key" type configuration such that carrier 124 can be inserted into the first port 110 in only one orientation. For example, carrier 124 can include a wedge-shaped corner 146 such that the carrier 124 can only fit into the first port 110 when the wedge-shaped corner 146 mates with the opening of the first port 110 in a certain orientation. This "key" type configuration may prompt the user as to the proper insertion orientation of the carrier and can prevent damage to the circuit board 126 caused by improper insertion.

Circuit board 126 includes a protocol processor 174, a memory chip 148, and a plurality of electrical contacts 138-144. These electrical contacts can include a voltage supply contact 138, a ground contact 140, a data input/output contact 142, and a clock contact 144. To enhance its reliability, ground contact 140 is of greater length. The circuit board 126 is mounted to the carrier 124 such that the ground contact 140 extends closer to distal end 130 than the other electrical contacts 138, 142, and 144. As a result, ground contact 140 is the first electrical contact on circuit board 126 to make electrical contact with the computer 112 when first data coupling 106 is inserted into first port 110 and the last electrical contact to break electrical contact with the computer 112 when first data coupling 106 is removed. This prevents the memory chip 148 from being powered in an unintended operating mode that may not be reliable.

Memory chip 148 is mounted on the circuit board 126 and stores the data in a predetermined format. Memory chip 148 can be a read only memory ("ROM"), random access memory ("RAM"), or both, and can store program instructions to implement various communication protocols. Preferably, memory chip 148 includes a non-volatile memory, so as to retain the stored data when un-powered. For example, memory chip 148 can be an electronically erasable programmable read only memory ("EEPROM") chip. Such EEPROM chips can typically be written to many times (e.g., one million write cycles, or more) so that it does not wear out over the life cycle of usage.

In one embodiment, a number of communication protocol drivers are stored in the read only memory of memory chip 148. An appropriate driver is chosen from the library of available communication protocol drivers when the first data coupling 106 is inserted into the first port 110 of the computer 112 and the second data coupling 116 is inserted into the second port 128 of the medical device 102. In another embodiment of the present invention, an appropriate communication protocol driver is downloaded from the medical device 102 connected to the smart interface assembly 104 and is stored in the random access memory.

Memory chip 148 can be electrically connected to the plurality of electrical contacts 138-144 on the circuit board 126. Accordingly, when the appropriate voltage is applied to voltage supply 138, relative to ground contact 140, data can be synchronously read from or written to the memory chip 148 using data input/output contact 142 and clock contact 144.

2. Auto-Execution Function of the Smart Interface Assembly

Figure 4:
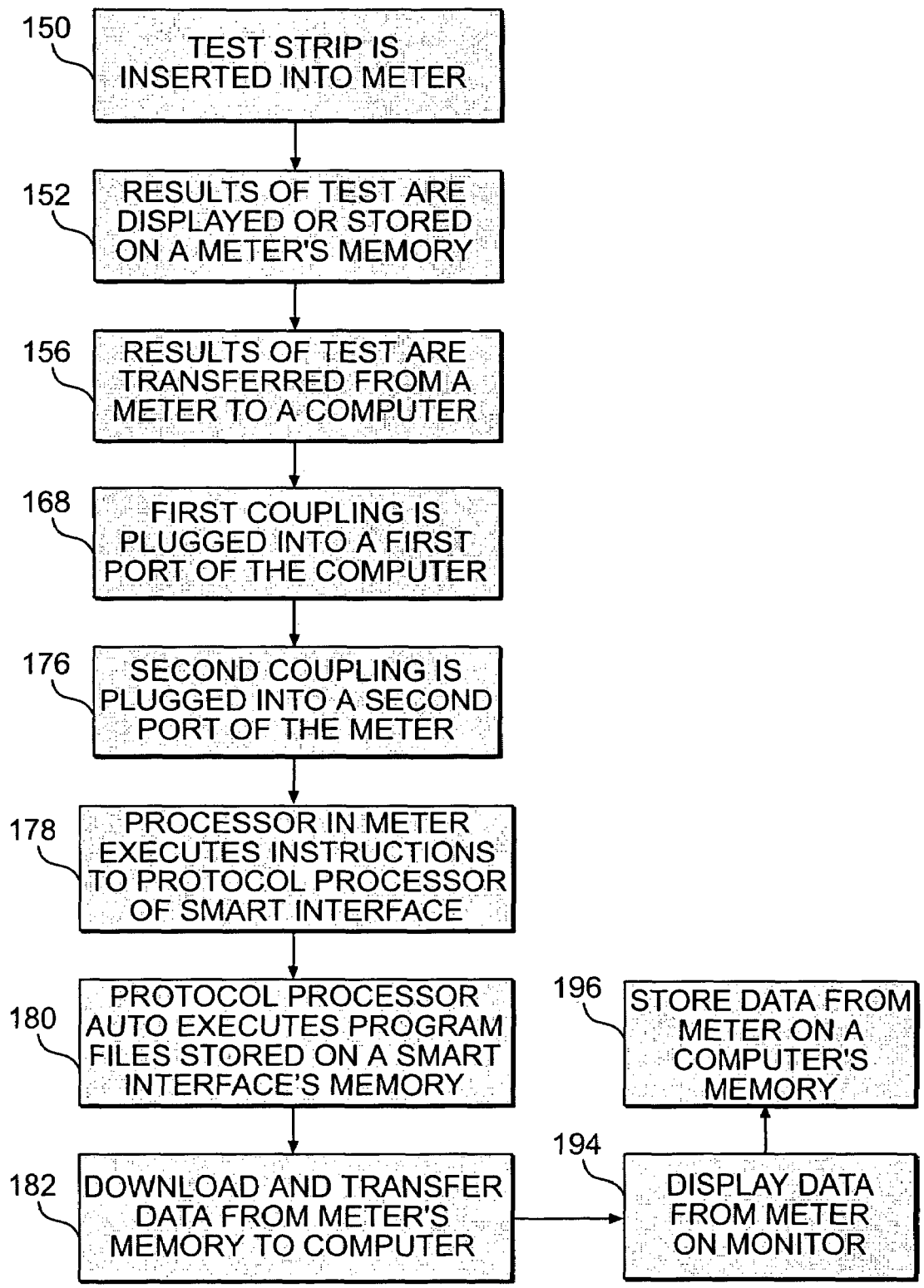
FIG. 4 is a flow chart illustrating a method of storing and auto-executing program files from a meter to a personal computer, in accordance with a preferred embodiment of the present invention.

The flowchart of FIG. 4 illustrates an exemplary read and write sequence starting from a medical device 102 to a computer 112. A user first inserts a test strip (not shown) into meter 102 to measure the amount of glucose in the blood, as indicated by step 150. In step 152, the meter 102 can then either display a message or an icon providing the user the results of the test or store the results in a memory 154, or both. A user may then want to display the diagnostic test results on a personal computer or transmit the results to a physician's computer. Thus, step 156 provides a method of transferring test results from the meter 102 to a computer 112.

A user first plugs in the first data coupling 106 into first port 110 of the computer 112 such that the first plurality of pins 108 make contact with electrical contacts 184-190 of a data coupling 192 of the computer 112, as indicated by step 168. In step 176, the second data coupling 116 is plugged into second port 128 of the meter 102 such that the second plurality of pins 118 make contact with electrical contacts 158-164 of a data coupling 166 of the meter 102. These electrical contacts can include a voltage supply contact 158, a ground contact 160, a data input/output contact 162, and a clock contact 164. Once connected, in step 178, a processor 170 within a microcontroller 172 of the meter 102 executes machine language instructions to a protocol processor 174 mounted on circuit board 126. Upon receiving the instructions, in step 180, protocol processor 174 auto-executes application program files stored within the memory 148 of the smart interface assembly 104. The hardware and software of the medical device 102 and smart interface assembly 104 work together to automatically configure the smart interface assembly, assign resources, and allow for hardware changes and additions without complicated setup maneuvers.

The smart interface assembly 104 of the present invention automatically determines which communication protocols are required at each of its ports, and selects, activates, enables, or downloads the appropriate communication protocol drivers to enable proper operation. In step 182, electrical contacts 138-144 access the memory 154 within the meter 102 and transmit the desired data to a processor 198 within a microcontroller 200 of the computer 112. As is known to one skilled in the art, a data interface can provide for the transfer of data to the computer 112. Thus, in the present invention, smart interface assembly 104 also serves as a data interface for transferring data from the meter 102 to the computer 112. Furthermore, it will be understood that the present invention is not limited to any particular type of data that is transferred from the medical device 102 to the computer 112. Data such as test results, charts, graphs, trends, software application programs, etc. may be transferred consistent with the principles of the present invention. After all of data has been transferred from the memory 154 of the meter 102 to computer 112, the incoming data from the meter can either be displayed on a monitor 114, step 194, or stored in a memory 206 within the computer 112 to be analyzed at a later, more convenient time, step 196.

The data transferred from the electronic meter can optionally be encrypted with identification information, including for example a serial number or name identifier of the meter, a user name, or other identifying data. Optionally, the device and patient identification data can be transmitted from the meter together or sequentially, along with the diagnostic test data, such that the computer software recognizes which data belongs with which user. Such an arrangement would be advantageous in settings such as a pharmacy, where insurance or other reimbursement for test strips is conditioned upon proof of a user's regular testing. The ability to correlate data with an identifiable user would also be useful for physicians, as well as in any setting where multiple users live, work or frequent.

Figure 5:
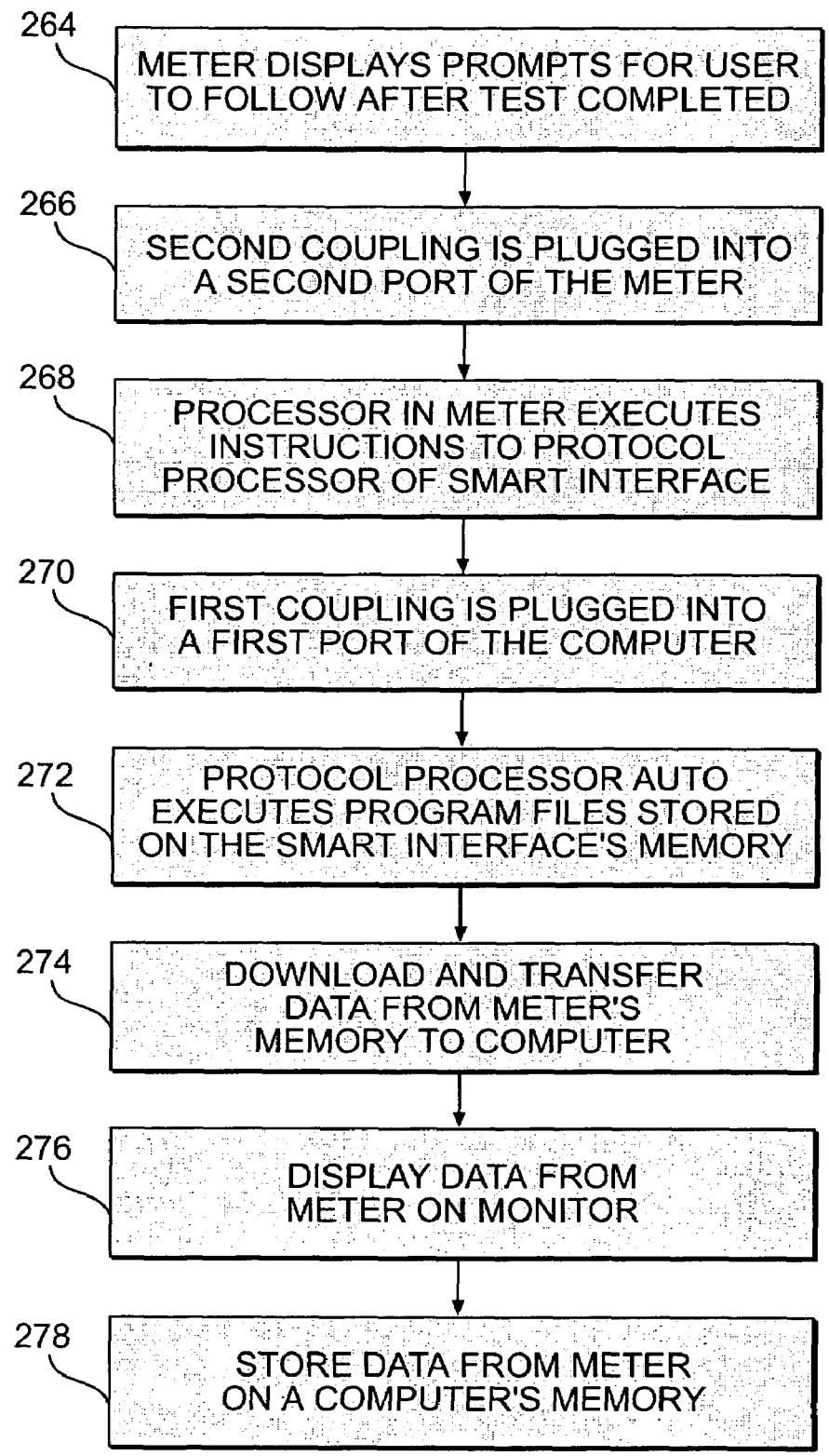
FIG. 5 is a flow chart illustrating an alternate method of storing and auto-executing program files from a meter to a personal computer, in accordance with a preferred embodiment of the present invention.

In another exemplary embodiment of the invention, the flowchart of FIG. 5 illustrates an additional method where the PC 112 can interface directly with the meter's memory 154 through the smart interface assembly 104.

A user can optionally follow prompts on the meter display 234 after the results of the diagnostic test are complete, as indicated by step 264. The user first plugs in the second data coupling 116 into the second port 128 of the meter 102 such that the second plurality of pins 118 make contact with electrical contacts 158-164 of the data coupling 166 of the meter 102, step 266. In step 268, once connected, the circuit 126 of the smart interface 104 handshakes with a processor 170 within a microcontroller 172 of the meter 102 to execute machine language instructions and to complete the connection of the meter 102 to the interface 104, for instance through a protocol processor 174 within the circuit board 126 of the smart interface assembly 104. The meter 102 and interface 104 combination then form a composite device. In step 270, optionally following a prompt on the meter display 234, the user can then plug in the first USB data coupling 106 into the first port 110 of a computer 112 such that the first plurality of pins 108 make contact with electrical contacts 184-190 of a data coupling 192 of the computer 112. The computer 112 recognizes the interface 104 and meter 102 assembly, for example through Plug-and-Play protocols, and can execute interface software contained resident on the interface 104. For example, the protocol processor 174 can be configured to auto-execute application program files stored in the smart interface memory 148, and electrical contacts 138-144 on the circuit board 126 access a memory 154 within the meter 102, step 272. As above, the desired data can then be transmitted from the meter's memory—154 directly to a processor 198 within a microcontroller 200 of the computer 112, step 274, or in step 276, the data can either be displayed on the computer's monitor 114 or stored in the memory 206, step 278.

Figure 6:
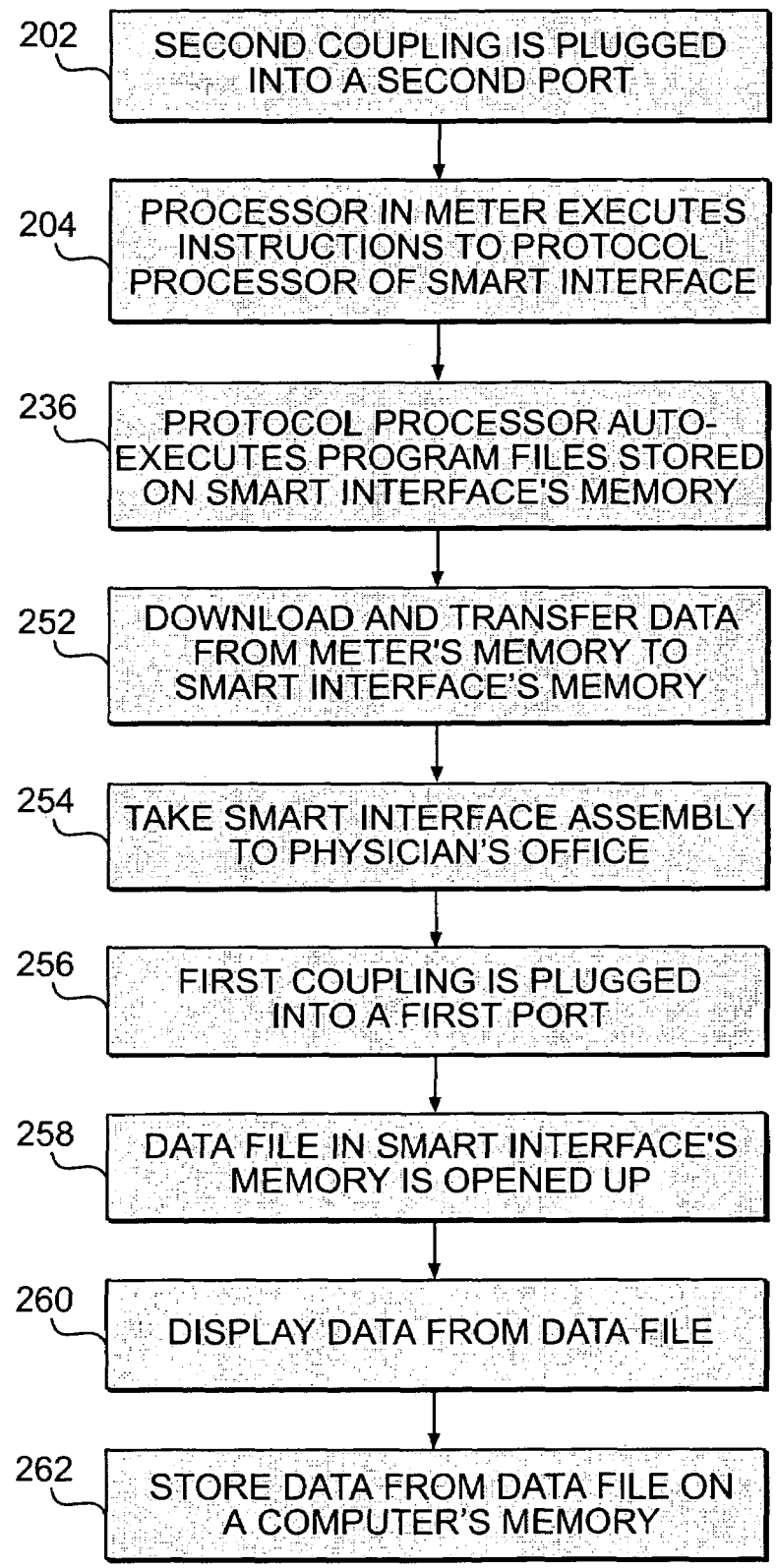
FIG. 6 is a flow chart illustrating a method of storing and auto-executing program files from a meter to a smart interface assembly, in accordance with a preferred embodiment of the present invention.

In yet another embodiment of the present invention, a user can transport the lightweight, smart interface assembly 104 to a computer for viewing data and analysis without having to bring meter 102 along. The flowchart of FIG. 6 illustrates an exemplary read and write sequence starting from a meter 102 to the smart interface assembly 104, where data can be stored on the interface assembly 104.

Similar to the process described above, in step 202, a user plugs in the second data coupling 116 into the second port 128 of the meter 102 such that the second plurality of pins 118 make contact with electrical contacts 158-164 of a data coupling 166 of the meter 102. Once connected, a processor 170 within a microcontroller 172 of the meter 102 executes machine language instructions to a protocol processor 174 mounted on circuit board 126, as indicated by step 204. Upon receiving the instructions, in step 236, protocol processor 174 auto-executes application program files stored within the smart interface memory 148 and electrical contacts 138-144 start transferring data from the memory 154 of the meter 102 to the memory chip 148 of the smart interface assembly 104, step 252. After all of the desired data has been downloaded to the memory chip 148 of the smart interface assembly 104, the user is now able to take the lightweight, smart interface 104 to a physician's office or a computer in a remote location, as indicated by step 254. It should be noted that after data is transferred from the memory 154 of the meter 102 to the memory chip 148 of the smart interface assembly 104, a user has an option of erasing some or all of the data stored in the meter's memory 154 such that more storage space is available for diagnostic tests in the future.

Next, at a physician's office, for example, the user can plug in the first USB data coupling 106 of the smart interface assembly 104 into the first port 110 of computer 112, such that the first plurality of pins 108 make contact with electrical contacts 184-190 of a data coupling 192 of the computer 112, step 256. Once connected, the smart interface assembly 104 serves as a well known jump drive, memory key, or any other memory device of similar type. In step 258, a physician can open up the desired data file from the memory 148 of the smart interface assembly 104 and either display the test results on the monitor 114, step 260, or store the data in the computer's memory 206, such that the results can be reviewed at a later time, as indicated by step 262.

3. Meter Electronics

Figure 7:
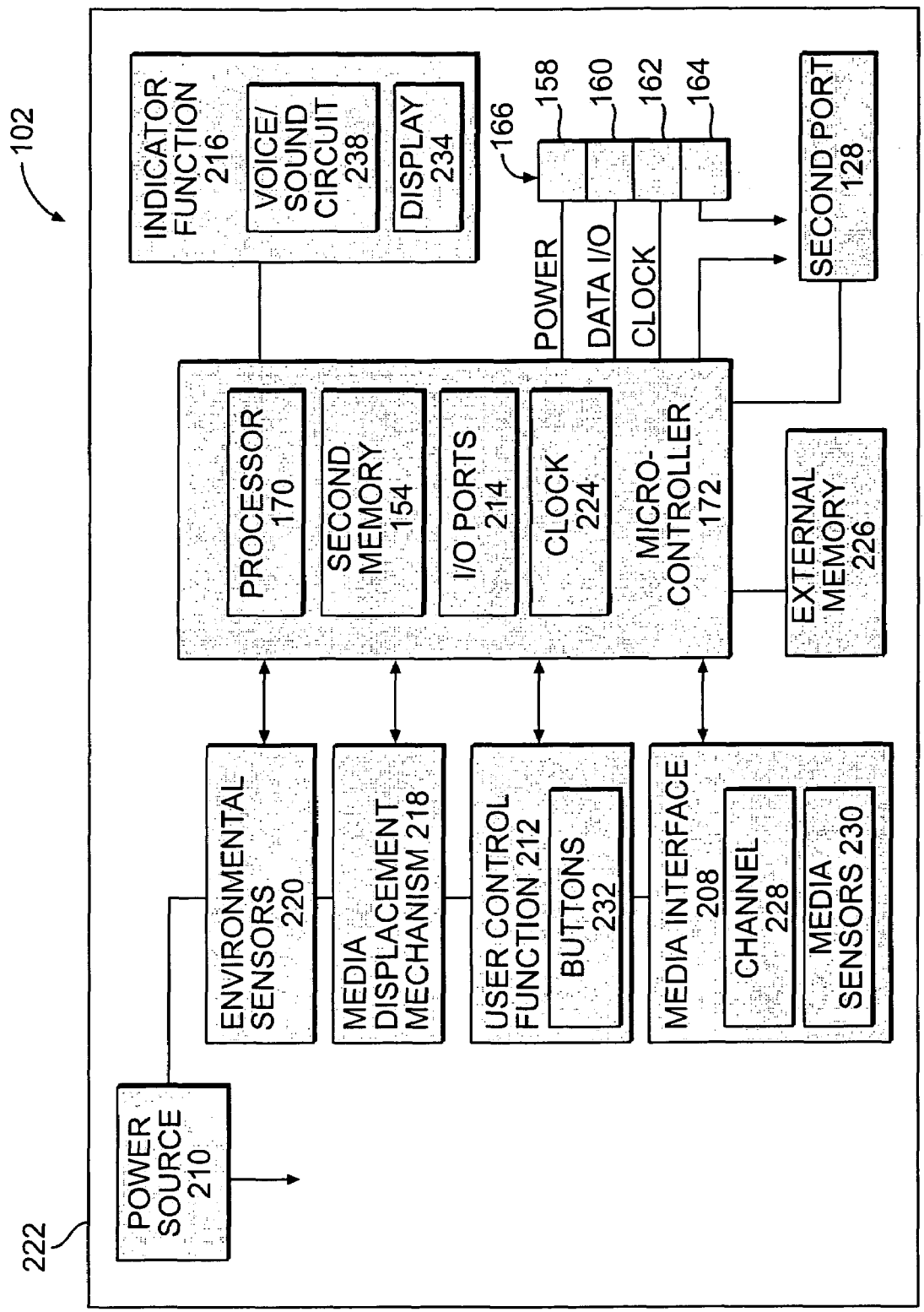
FIG. 7 illustrates an exemplary block diagram of an electronic meter, in accordance with a preferred embodiment of the present invention.

As described above, to measure the glucose level in a blood sample, a test strip (not shown) is preferably used with an electronic meter 102, as shown in FIGS. 1 and 7. FIG. 7 shows, in simplified form, a block diagram illustrating functional components of exemplary electronic meter 102. Meter 102 can include a second port 128, a data coupling 166, an indicator function 216, a microcontroller function 172, an external memory 226, a media interface 208, a user control function 212, a media dispensing mechanism 218, environmental sensors 220, and a power source 210. In an illustrative embodiment, the functional components of meter 102 are contained within meter housing 222.

Microcontroller 172 controls the operation of the functional components of the meter in accordance with its instructions, which can be provided as software or firmware. Microcontroller 172 can include the processor 170, memory 154, clock functions 224, and input/output ports 214. In an illustrative embodiment of the invention, the processor 170, memory 154, clock 224 functions, and/or input/output ports 214 can be implemented using an Application Specific Integrated Circuit (ASIC), which allows microcontroller 172 to be reduced in size in comparison to standard integrated circuit technology. However, it will be understood that the microcontroller 172 can be implemented using standard integrated circuit technology, or other technology, without departing from the scope of the present invention.

Processor function 170 executes instructions used to control the functional components of meter 102. In particular, processor 170 executes instructions necessary to perform the diagnostic test. A plurality of machine language instructions for the processor 170 can be stored in the memory 154, an external memory 226, or the memory chip 148 of the smart interface assembly 104. The memory 154 can also store data, such as calibration data and other data, used in the performance of the diagnostic tests.

Clock function 224 regulates the processor's execution of the instructions in time. In particular, clock function 224 is used to regulate the timing of steps in the diagnostic test. For instance, processor 170 can use clock 224 to regulate an incubation time period, or other time periods, necessary for the correct performance of the diagnostic test. Clock function 224 can be implemented by a single system clock or by multiple clocks for different purposes.

Media interface 208 accepts test media, such as test strips (not shown), and includes a channel 228 to ensure that the test media is correctly positioned when inserted by a user or media dispensing mechanism 218. Interface 208 includes one or more media sensors 230 for determining, e.g., whether a test strip has been correctly inserted in the channel 228. For meters using electrochemical techniques, the media sensors 230 can include one or more electrical contacts corresponding to electrodes on an interface side of the test strip. For meters using photometric techniques, at least the presence or concentration of analyte in the sample is determined using an optical sensor, e.g., a light emitting diode and corresponding photo-detector.

Power source 210 provides power to the electronic components of meter 102. In an illustrative embodiment, the power source is a lithium coin cell battery. However, other power sources, such as other types of batteries, solar cells, or AC/DC converters may be used without departing from the scope of the present invention.

User control function 212 can include, for example, one or more buttons, switches, keys or other controls for controlling the functions of meter 102. In an illustrative embodiment, user control function 212 is implemented by one or more buttons 232 placed on the left side of meter housing 222. However, user control 212 may be positioned elsewhere on meter 102. For example, button 232 can be placed on right hand side of the meter housing 222 in order to be more convenient for left handed users, or on the top of the meter.

In an exemplary embodiment of the present invention, user control function 212 is implemented using a single control, e.g., a single button 232, that is used to control a plurality of meter functions. For example, user control 212 can be used to control the input/output 214 function, indicator function 216, and/or media dispensing mechanism 218 by providing commands to these functions directly or through microcontroller 172. User control 212 can also be used to control the diagnostic test function of microcontroller 172. For example, when a test is to be performed using a control solution, button 232 may be held down to indicate to microcontroller 172 that the current sample is of a control solution and, consequently, that microcontroller 172 should perform a control test on the current strip.

Alternatively, a plurality of user controls 212, e.g., a plurality of buttons 232, can be provided, with each button having different functions. For example, two buttons may be provided to allow a user to scroll through diagnostic test results stored in the memory 154 in either forward or reverse directions. As an aid to the user, the function of the button or buttons 232 at the particular time can be dynamically indicated by indicator function 216. Further, user controls 212 can have different functions at different times. For example, holding button 232 down upon the insertion of a test strip into media interface 208 can command the microcontroller 172 to perform a control test on that strip, while holding the button 232 down without inserting a test strip can command the microcontroller 172 to display the result of the previous diagnostic test.

Input/output function 214 provides for the downloading of data or instructions to meter 102, and/or the uploading of data from meter 102. Input/output function 214 can be used, for example, to upload the results of a diagnostic test or tests so that they may be transferred to the smart interface assembly 104 or to a third party, e.g., a medical care provider for use in treating the user. Alternatively, input/output function 214 can be used to download data (e.g., calibration data) or instructions (e.g., updated software) to the meter 102. Input/output function 214 can be implemented using any conventional digital or analog information interface, e.g., a serial port, a parallel port, an optical port, an infrared interface, etc.

Indicator function 216 indicates the result of the diagnostic test to the user. In addition to indicating the result of the diagnostic test, the indicator can present other information to the user. For example, the indicator 216 may indicate the average result of a plurality of tests, the time and/or date, remaining battery life, etc. Indicator 216 can also be used to prompt the user to perform certain steps of the diagnostic test, e.g., to apply the sample to the test strip. In an exemplary embodiment of the present invention, indicator 216 indicates the number of tests or the time remaining before meter 102 becomes inoperative.

Indicator function 216 can present information in visible, audible or tactile form. For example, indicator 216 may include a display 234 for displaying information, e.g., using numerical values, words and/or icons. A number of different technologies may be used for display 234. For example, the display can be a liquid crystal display, a vacuum fluorescent display, an electroluminescent display, a light emitting diode display, a plasma display, etc. In an illustrative embodiment, display 234 is a liquid crystal display. Alternatively or in addition, indicator 216 can include an audible indicator configured to indicate information by sound. For example, indicator 216 may include a speaker connected to a voice and/or sound circuit 238 that is configured to, e.g., speak the result of the diagnostic test or to beep to indicate that an error has occurred. As a further alternative, indicator 216 can be implemented as a dynamic Braille indicator for use by the blind.

Because the diagnostic test media, e.g., test strips, are typically very small, certain users may find it difficult to retrieve the test media from a container. Accordingly, a media dispensing mechanism 218 may be used to provide for the automated dispensing of test media from the container.

4. Computer Electronics

Figure 8:
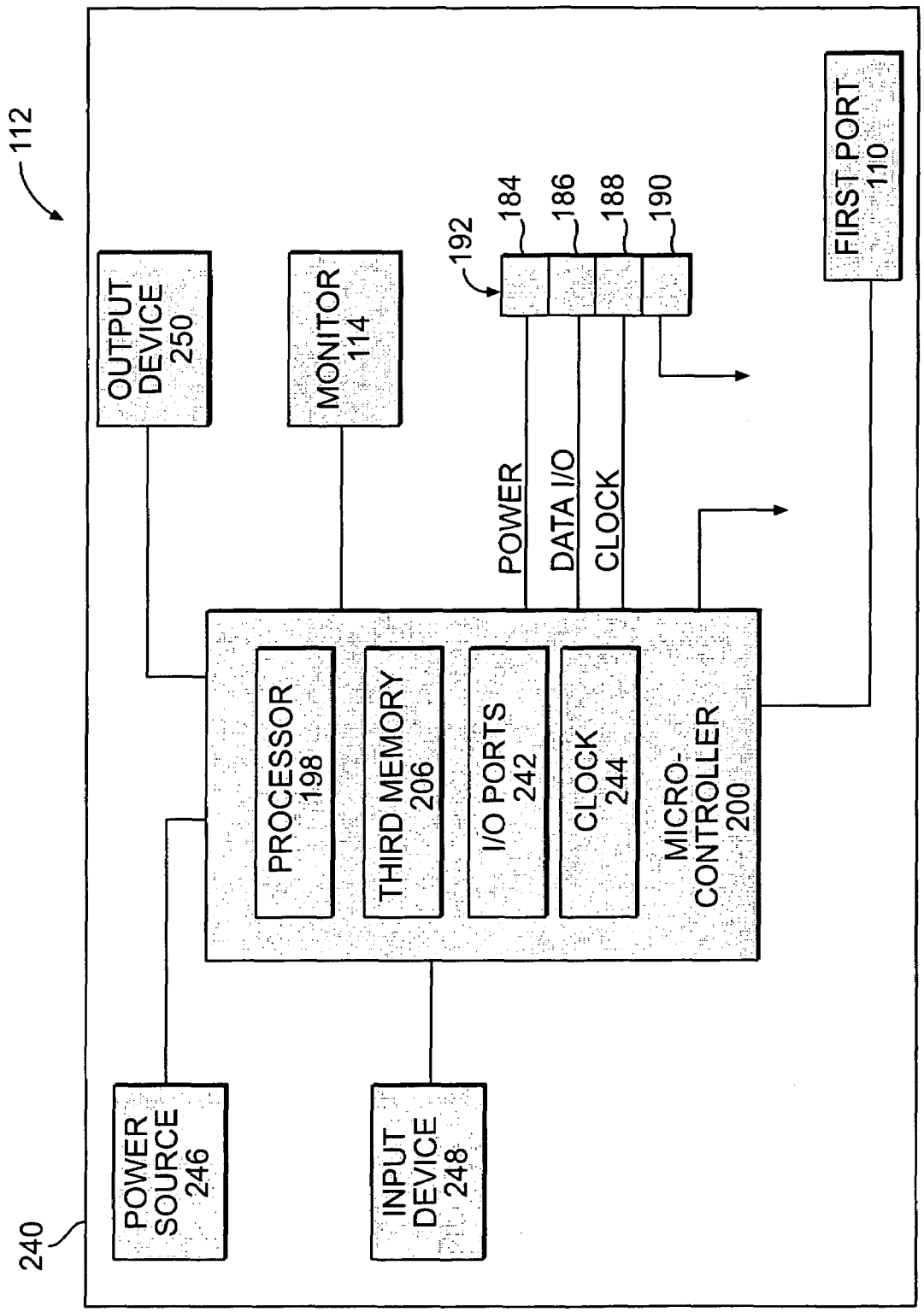
FIG. 8 is an exemplary block diagram of a computer, in accordance with a preferred embodiment of the present invention.

As described above, the computer 112 of diagnostic system 100 is a general-purpose computing system. FIG. 8 illustrates, in simplified form, a block diagram illustrating functional components of the computer 112. Computer 112 can include a power source 246, an input device 248, a microcontroller 200, an output device 250, a monitor 114, a data coupling 192, and a first port 110. Possible input devices 248 include network interfaces, keyboards, mice, speech recognition devices, or document, video, or image input devices. Additionally, possible output devices include network interfaces, printers, or sound or speech output devices. In an illustrative embodiment, the functional components of the computer 112 are contained within computer housing 240.

As illustrated in FIG. 8, the computer system 112 can also include at least one microcontroller or central processing unit ("CPU") 200. CPU 200 can execute software programs for implementing some of the processes described above with respect to FIGS. 4-6. Software programs for the computer system can reside in the third memory 206 of the CPU 200. Third memory 206 can include graphs, charts, etc., and software for manipulating the data.

Microcontroller 200 controls the operation of the functional components of the computer in accordance with its instructions, which can be provided as software or firmware. Microcontroller 200 can include a processor 198, third memory 206, input/output ports 242, and clock functions 244. These functional components operate similarly to the functional components of microcontroller 172 of meter 102, as described above.

The foregoing description of possible implementations consistent with the present invention does not represent a comprehensive list of all such implementations or all variations of the implementations described. The description of only some implementations should not be construed as an intent to exclude other implementations. One of ordinary skill in the art will understand how to implement the invention in the appended claims in many other ways, using equivalents and alternatives that do not depart from the scope of the following claims.

The systems and methods disclosed herein can be embodied in various forms. Moreover, the above-noted features and other aspects and principles of the present invention can be implemented in various environments. Such environments and related applications can be specially constructed for performing the various processes and operations according to the invention or they can include a general-purpose computer selectively activated or reconfigured by code to provide the necessary functionality. The processes disclosed herein are not inherently related to any particular computer or other apparatus, and can be implemented by a suitable combination of hardware, software, and/or firmware. For example, various general-purpose machines can be used with programs written in accordance with teachings of the invention, or it may be more convenient to construct a specialized apparatus or system to perform the required methods and techniques.

Additional benefits are possible through use of the smart interface of the present invention. For instance, when connected to a computer, software or firmware updates for the meter can be obtained and installed automatically from a manufacturer's web site, using, for instance, simple HTTP protocols.

Of course, it should be appreciated that while discussion of exemplary embodiments places certain functionalities and memory storage locations either within the interface or in the meter, placement of these functions in one or the other location is not always critical to the invention. For the interface to serve as a standalone device, one having ordinary skill in the art would appreciate that certain functionality would need to be located on the interface, but the functionality of the composite interface and meter combination described hereinabove could be enabled where all functionality is provided on the meter, and the interface is employed essentially for data connectivity between the computer and the meter, similar to a digital camera or digital media player.

Systems and methods consistent with the present invention also include computer readable media that include program instruction or code for performing various computer-implemented operations based on the methods and processes of the invention. The media and program instructions can be those specially designed and constructed for the purposes of the invention, or they can be of the kind well known and available to those having skill in the computer software arts.

What is claimed is:

1. A medical diagnostic testing system for providing diagnostic data to a computer having a first port, comprising:
    a diagnostic testing device having a second port; and
    a computer interface assembly comprising:
        a first data coupling capable of establishing data communication with the first port of the computer;
        a second data coupling capable of establishing data communication with the second port of the diagnostic testing device; and
        a connecting portion joining the first data coupling with the second data coupling, the connecting portion further comprising a connecting processor and a memory;
    wherein the connecting processor automatically determines which protocol driver is required at the first and second ports to enable communication between the diagnostic testing device and the computer.

2. The medical diagnostic testing system of claim 1, wherein the diagnostic testing device is a blood glucose meter.

3. The medical diagnostic testing system of claim 1, wherein at least one of the first and second data couplings comprises a plug.

4. The medical diagnostic testing system of claim 3, wherein the plug is a USB connector.

5. The medical diagnostic testing system of claim 3, wherein the plug is a IEEE 1394 connector.

6. The medical diagnostic testing system of claim 3, wherein the plug is a serial connector.

7. The medical diagnostic testing system of claim 1, wherein at least one of the first and second data couplings comprises a wireless communications device.

8. The medical diagnostic testing system of claim 7, wherein the wireless communications device comprises an infrared device.

9. The medical diagnostic testing system of claim 8, wherein the infrared device operates on a wavelength in a range of about 850 nm to about 1050 nm.

10. The medical diagnostic testing system of claim 7, wherein the wireless communications device comprises an RF frequency device.

11. The medical diagnostic testing system of claim 10, wherein the RF frequency device operates in a range of about 2.4 GHz to about 2.48 GHz.

12. The medical diagnostic testing system of claim 10, wherein the RF device is enabled for spread spectrum operation.

13. The medical diagnostic testing system of claim 10, wherein the RF device is enabled frequency hopping operation.

14. The medical diagnostic testing system of claim 10, wherein the RF device is enabled for full-duplex operation.

15. The medical diagnostic testing system of claim 13, wherein the RF device is enabled for operation up to 1600 hops/sec.

16. The medical diagnostic testing system of claim 13, wherein a signal hops among 79 frequencies at 1 MHz intervals.

17. The medical diagnostic testing system of claim 10, wherein the RF device has an output of about 0 dBm (1 mW).

18. The medical diagnostic testing system of claim 10, wherein the RF device has an output in a range of −30 to +20 dBm (100 mW).

19. The medical diagnostic testing system of claim 1, wherein the memory is configured to contain machine instruction code for execution on the computer.

20. The medical diagnostic testing system of claim 19, wherein the machine instruction code comprises software to process test results from the diagnostic testing device on the computer.

21. The medical diagnostic testing system of claim 1, wherein the connecting portion comprises a cable.

22. The medical diagnostic testing system of claim 1, wherein the connecting portion comprises a housing.

23. The medical diagnostic testing system of claim 1, wherein the connecting portion comprises a circuit carrier.

24. A method for providing diagnostic data to a computer having a first port, the method comprising:
    a) providing a diagnostic testing device comprising a second port;
    b) providing a smart interface assembly to transmit at least one test value to the computer, the smart interface assembly comprising:

i) a first data coupling capable of establishing data communication with the first port of the computer;
ii) a second data coupling capable of establishing data communication with the second port of the diagnostic testing device; and
iii) a connecting portion joining the first data coupling with the second data coupling, the connecting portion further comprising a connecting processor and a memory,
wherein the connecting processor automatically determines which protocol driver is required at the first and second ports to enable communication between the diagnostic testing device and the computer;
c) performing a diagnostic test on the diagnostic testing device to obtain at least one test value; and
d) transmitting the at least one test value from the diagnostic testing device to the computer.

25. The method of claim 24, further comprising the step of hard wiring a connection between the data communication port of the meter and the second data coupling of the smart interface device.

26. The method of claim 24, further comprising the step of plugging in a connection between the data communication port of the meter and the second data coupling of the smart interface device.

27. The method of claim 24, further comprising the step of completing a wireless connection between the data communication port of the meter and the second data coupling of the smart interface device.

28. The method of claim 24, further comprising the step of hard wiring a connection between the computer and the first data coupling of the smart interface device.

29. The method of claim 24, further comprising the step of plugging in a connection between the computer and the first data coupling of the smart interface device.

30. The method of claim 24, further comprising the step of completing a wireless connection between the computer and the first data coupling of the smart interface device.

31. The method of claim 24, wherein the step of providing the diagnostic testing device comprises providing a blood glucose meter.

32. The method of claim 24, further comprising the step of executing machine instruction code on the smart interface device on the computer.

33. The method of claim 32, wherein the executing step further comprises processing the at least one test value from the diagnostic testing device on the computer.

34. The method of claim 24, wherein the connecting portion in said providing step comprises a cable.

35. The method of claim 24, wherein the connecting portion in said providing step comprises a housing.

36. The method of claim 24, wherein the connecting portion in said providing step comprises a circuit carrier.

37. The method of claim 24, further comprising the step of transmitting identification information.

* * * * *